(12) United States Patent
Freedman et al.

(10) Patent No.: US 7,967,810 B2
(45) Date of Patent: Jun. 28, 2011

(54) SUB-ATMOSPHERIC WOUND-CARE SYSTEM

(75) Inventors: Brett A. Freedman, Decatur, GA (US); Robert L. Pauly, Friendswood, TX (US)

(73) Assignee: Mary Beth Kelley, New York, NY (US)

( * ) Notice: Subject to any disclaimer, the term of this patent is extended or adjusted under 35 U.S.C. 154(b) by 174 days.

(21) Appl. No.: 11/875,668

(22) Filed: Oct. 19, 2007

(65) Prior Publication Data

US 2008/0300578 A1  Dec. 4, 2008

Related U.S. Application Data

(60) Provisional application No. 60/853,000, filed on Oct. 20, 2006.

(51) Int. Cl.
*A61M 27/00* (2006.01)

(52) U.S. Cl. .......... 604/543; 604/35; 604/305; 604/306; 604/307; 604/308; 604/317; 604/318; 604/319; 604/320; 604/321; 604/322; 604/323; 604/540; 604/541; 604/542; 604/544; 604/902; 606/131

(58) Field of Classification Search .......... 604/540–544
See application file for complete search history.

(56) References Cited

U.S. PATENT DOCUMENTS

| | | | |
|---|---|---|---|
| 4,460,354 A | 7/1984 | Weilbacher et al. | |
| 4,559,035 A | 12/1985 | Benjamin et al. | |
| 4,969,880 A | 11/1990 | Zamierowski | |
| 5,071,409 A * | 12/1991 | Rosenberg | 604/119 |
| 5,100,396 A | 3/1992 | Zamierowski | |
| 5,261,893 A | 11/1993 | Zamierowski | |
| 5,527,293 A | 6/1996 | Zamierowski | |
| 5,549,584 A | 8/1996 | Gross | |
| 5,636,643 A | 6/1997 | Argenta et al. | |
| 5,645,081 A | 7/1997 | Argenta et al. | |
| 5,678,564 A | 10/1997 | Lawrence et al. | |
| 5,911,222 A | 6/1999 | Lawrence et al. | |
| 6,045,541 A | 4/2000 | Matsumoto et al. | |
| 6,048,337 A | 4/2000 | Svedman | |
| 6,071,267 A | 6/2000 | Zamierowski | |
| 6,142,982 A | 11/2000 | Hunt et al. | |
| 6,345,623 B1 | 2/2002 | Heaton et al. | |
| 6,458,109 B1 | 10/2002 | Henley et al. | |

(Continued)

OTHER PUBLICATIONS

B.M. Kostiuchenok et al.; "The Vacuum Effect in the Surgical Treatment of Purulent Wounds"; included in The Kremlin Papers, Perspectives in Wound Care from the Russian Medical Journal: Vestnik Khirurgii; Sep. 1986; pp. 18-21; BlueSky Publishing, 6965 El Camino Ste 105-902 LaCosta, CA 92009.

(Continued)

*Primary Examiner* — Tatyana Zalukaeva
*Assistant Examiner* — Ilya Y Treyger
(74) *Attorney, Agent, or Firm* — The Brevetto Law Group

(57) ABSTRACT

Methods and systems are provided for a sub-atmospheric wound-care (SAWS) system for treating an open wound. The SAWS system includes a regulated vacuum source for developing a negative pressure, a flow rate meter configured to measure a flow rate of liquid removed from the wound, a primary pressure regulating sensor located proximate the wound for directly measuring the negative pressure at the wound, a backup pressure regulating sensor located vacuum tube, a porous dressing suitable to be sealed airtight which is positioned within a wound interface chamber, a collection canister configured to collect said liquid removed from the wound, and an adapter configured to use wall suction a primary regulated vacuum source.

20 Claims, 4 Drawing Sheets

300

U.S. PATENT DOCUMENTS

| | | | |
|---|---|---|---|
| 6,468,237 | B1 | 10/2002 | Lina |
| 6,695,823 | B1 | 2/2004 | Lina et al. |
| 6,767,334 | B1 | 7/2004 | Randolph |
| 7,004,915 | B2 | 2/2006 | Boynton et al. |
| 7,117,869 | B2 | 10/2006 | Heaton et al. |
| 7,276,051 | B1 | 10/2007 | Henley et al. |
| 7,361,184 | B2 | 4/2008 | Joshi |
| 7,413,571 | B2 | 8/2008 | Zamierowski |
| 7,438,705 | B2 | 10/2008 | Karpowicz et al. |
| 7,520,872 | B2 | 4/2009 | Biggie et al. |
| 7,524,286 | B2 | 4/2009 | Johnson |
| 2002/0115967 | A1 | 8/2002 | Svedman |
| 2002/0183702 | A1 | 12/2002 | Henley et al. |
| 2003/0139255 | A1 | 7/2003 | Lina |
| 2003/0208149 | A1 | 11/2003 | Coffey |
| 2004/0006319 | A1 | 1/2004 | Lina et al. |
| 2004/0054338 | A1 | 3/2004 | Bybordi et al. |
| 2004/0064111 | A1 | 4/2004 | Lockwood et al. |
| 2004/0064132 | A1 | 4/2004 | Boehringer et al. |

OTHER PUBLICATIONS

Prof. Yu. A. Davydov et al.; "Vacuum Therapy in the Treatment of Purulent Lactation Mastitis"; included in The Kremlin Papers, Perspectives in Wound Care from the Russian Medical Journal: Vestnik Khirurgii; Sep. 1986; pp. 66-70; BlueSky Publishing, 6965 El Camino Ste 105-902 LaCosta, CA 92009.

Y.N. Usupov et al.; "Active Wound Drainage"; included in The Kremlin Papers, Perspectives in Wound Care from the Russian Medical Journal: Vestnik Khirurgii; Apr. 1987; pp. 42-45; BlueSky Publishing, 6965 El Camino Ste 105-902 LaCosta, CA 92009.

Prof. Yu. A. Davydov et al.; "The Bacteriological and Cytological Assessment of Vacuum Therapy of Purulent Wounds"; included in The Kremlin Papers, Perspectives in Wound Care from the Russian Medical Journal: Vestnik Khirurgii; Oct. 1988; pp. 48-52; BlueSky Publishing, 6965 El Camino Ste 105-902 LaCosta, CA 92009.

Prof. Yu. A. Davydov et al.; "Concepts for Clinical Biological Management of the Wound Process in the Treatment of Purulent Wounds Using Vacuum Therapy"; included in The Kremlin Papers, Perspectives in Wound Care from the Russian Medical Journal: Vestnik Khirurgii; Feb. 1991; pp. 132-135; BlueSky Publishing, 6965 El Camino Ste 105-902 LaCosta, CA 92009.

Bridgett L. Buckman; "Vacuum Assisted Wound Closure System"; Drexel University white paper; Jul. 15, 2006.

Angelica Wackenfors, MSc, et al.; "Effects of vacuum-assisted closure therapy on inguinal wound edge microvascular blood flow"; 2004; Wound Repair and Regeneration, vol. 12, No. 6, pp. 600-606; ISSN: 1067-1927.

Louis C. Argenta et al.; "Vacuum-Assisted Closure: A New Method for Wound Control and Treatment: Clinical Experience" 1997; Annals of Plastic Surgery, vol. 38, No. 6, pp. 563-577, Jun. 1997; Lipincott-Raven Publishers.

Louis C. Argenta et al.; "Vacuum-Assisted Closure: A New Method for Wound Control and Treatment: Basic Foundation" 1997; Annals of Plastic Surgery, vol. 38, No. 6, pp. 553-562, Jun. 1997; Lipincott-Raven Publishers.

Brock WB et al.; "Temporary Closrue of Open Abdominal Wounds: the Vacuum Pack"; Jan. 1995; Am Surg. Jan. 1995, vol. 61, No. 1, pp. 30-35.

Andrea L. Valenta; "Using the Vacuum Dressing Alternative for Difficult Wounds"; American Journal of Nursing, Apr. 1994, pp. 44-45.

\* cited by examiner

300

SUB-ATMOSPHERIC WOUND-CARE SYSTEM

CROSS-REFERENCE TO RELATED APPLICATIONS

The present application claims priority from, and incorporates by reference in its entirety, U.S. provisional patent application 60/853,000 filed Oct. 20, 2006.

BACKGROUND

1. Field of the Invention

The present invention relates to patient wound care, and more specifically to systems and methods of wound coverings and dressings.

2. Description of Related Art

The use of negative pressure or vacuum to heal wounds has gained great acceptance over the last 2 decades. Negative-pressure wound therapy involves the application of a vacuum to a sealed wound dressing in order to facilitate the heating properties of an open traumatic or chronic soft tissue wound. These types of wounds occur acutely from injury or as part of a chronic disease, like diabetes mellitus. An open wound is a wound that is not able to be closed side-to-side by direct suture repair for some reason. These reasons include but are not limited to the dimensions/size of the wound, the level of contamination or infection in the wound. Wounds of this sort are very common in combat casualties. They represent the single most common injury pattern seen in soldiers elevated to Echelon V level of healthcare.

While the value of vacuum assisted wound healing has been known for nearly one-half century, this form of wound care technology was first marketed in the U.S. market in the early 90's by Kinetic Concepts, Inc. (KCI)—the Wound V.A.C. More recently, Blue Sky Medical, Inc. has released a negative pressure wound therapy device, the Versatile 1, which is based on concepts of negative pressure therapy that were publicly known. Both the KCI and Blue Sky Medical products, however, are subject to several key deficiencies. These deficiencies of conventional devices have apparently not been recognized as problems in the art, since they remain unaddressed.

A negative pressure wound care device typically includes a regulated vacuum source, tubing and collection canisters, and a porous dressing that can be sealed airtight. Negative-pressure wound systems are used to treat open wounds either chronic as seen in conditions like diabetes or acute from trauma. Traditionally these wounds were treated with cotton gauze dressings which had to be changed three times per day. These changes were very painful to the patient and cost a significant amount of nurse and/or doctor labor hours. On the other hand, vacuum wound dressings can be left in place for several days, they are changed in the operating room (OR) so the patient is not awake and they essentially take care of themselves. This form of dressing reduces labor consumption and accelerates wound healing, often by 50% or more. However, conventional vacuum wound care devices are subject to a number of drawbacks giving rise to false failure alarm and increased susceptibility to patient infections.

SUMMARY

Embodiments disclosed herein address the above stated needs by providing systems and methods for a sub-atmospheric wound-care (SAWS) system for treating an open wound. Various embodiments of the SAWS system include a regulated vacuum source configured to develop a negative pressure, a flow rate meter configured to measure a flow rate of liquid removed from the wound, a pressure regulating sensor configured to be located proximate the wound for directly measuring the negative pressure at the wound, a collection canisters configured to collect said liquid removed from the wound, a porous dressing suitable to be sealed airtight, and an adapter configured to use wall suction a primary regulated vacuum source.

Other embodiments provide a brushless vacuum motor for use as a second regulated vacuum source, and a valve to switch between the first regulated vacuum source and the second regulated vacuum source. Various embodiments provide an electronic-programmable vacuum regulator which access the vacuum path between the wound interface chamber and the regulated vacuum source. The electronic-programmable vacuum regulator serves as the controller for the SAWS system.

BRIEF DESCRIPTION OF THE DRAWINGS

The accompanying drawings, which are incorporated in and constitute part of the specification, illustrate various embodiments of the invention. Together with the general description, the drawings serve to explain the principles of the invention. In the drawings.

DETAILED DESCRIPTION

Figure 1:
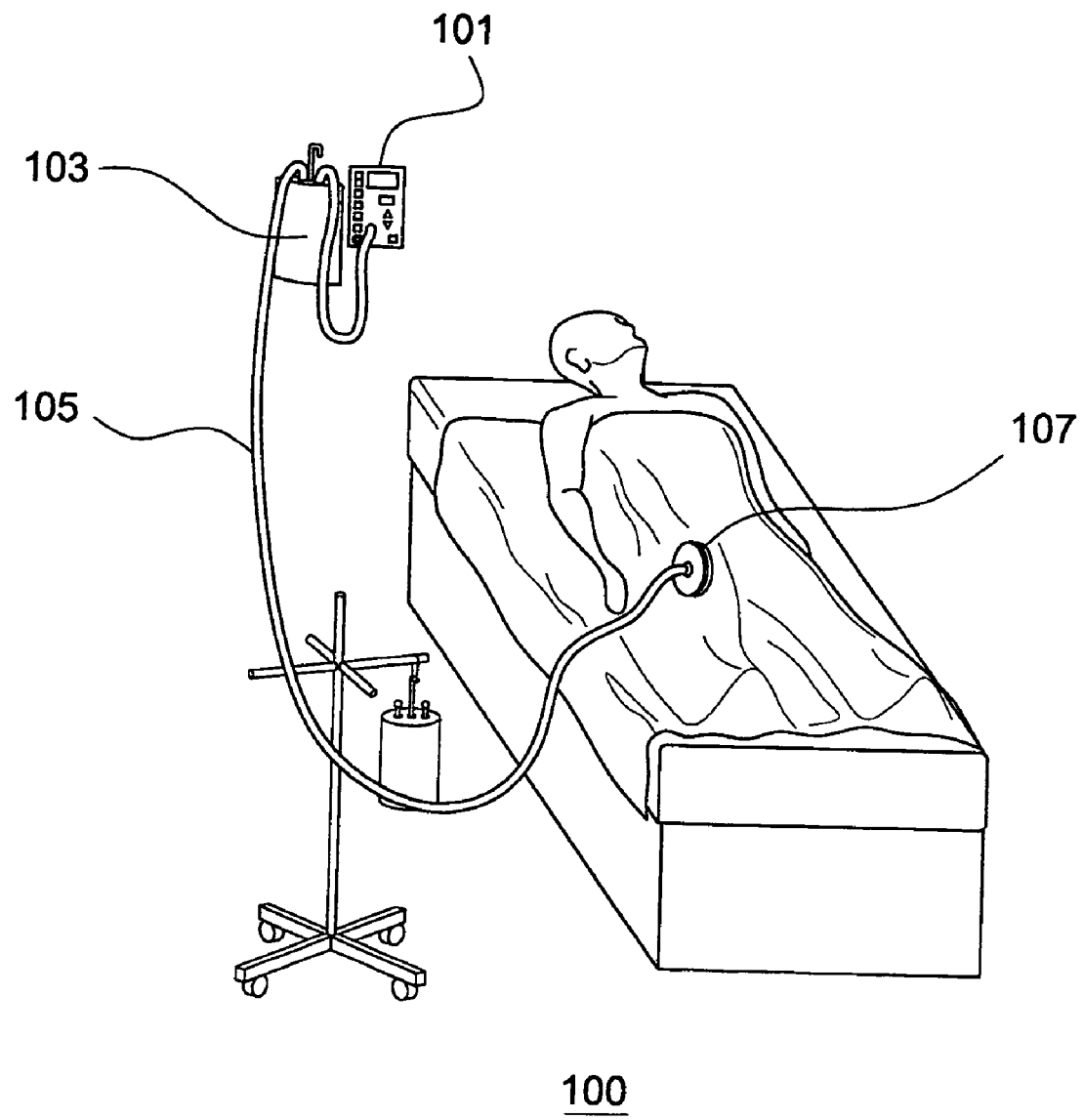
FIG. 1 depicts an exemplary embodiment of the Sub-Atmospheric Wound-care System in a typical clinical setting.

FIG. 1 depicts an exemplary embodiment 100 of the Sub-Atmospheric Wound-care System (SAWS) in a typical clinical setting. Various embodiments of the present invention adopt novel and useful approaches, as compared to conventional devices, for each of three components of the SAWS negative pressure wound care system.

Various embodiments of SAWS are configured with a flow rate meter 101 to measure the flow rate of liquid removed from the wound. This helps to avoid the danger of unwitnessed exsanguination, a rare but potentially lethal threat with conventional devices which have no early means for detecting accelerated fluid outflow from the wound. For example, in situations where an injured artery starts to bleed under the wound dressing, conventional devices have no similar dedicated warning system. Without a flow meter 101 and high flow alarm, conventional devices have no means for alerting medical staff to a potential vascular leak or exsanguination event. Problems such as conventional devices suctioning sanguineous fluid from arterial leaks are not detected until the collection canister of the conventional device is full. This delayed response system can significantly compromise a patients outcome following a vascular leak under a placed negative pressure dressing. The recorded flow rates provide a valuable metric for physicians, and gathering this type of data is an improvement in the use of negative pressure wound care systems.

The provision of the flow meter 101 in the SAWS device allows for the use of larger canisters 103, since warning alarms no longer need to depend on the canister filling to capacity. Typically, the canisters on conventional devices are small (e.g., 250 cc). The SAWS device may be equipped with larger, more economical generic sized canisters 103 (e.g., 1,000 cc) since SAWS has a flow meter 101 to detect excessive fluid flow rates. This helps to reduce nursing demands. Moreover, canister changes require that the suction is turned off for as much as 15 minutes. Turning suction off to the dressing during this period risks leaking wound fluid onto the adhesive seal, ultimately, ruining its adhesion and requiring replacement of the entire dressing. Thus, the larger canisters 103 of SAWS, which require fewer canister changes, aids in wound care. Various sizes of canisters may be used with SAWS, in addition to (or in place of) the 1000 cc canister. Typically, the canisters are made of clear plastic with markings every 100 cc. Specialized appendages may be provided to improve ergonomics and docking capability with the main EVR. The casing of the SAWS device is typically implemented with specialized appendages that securely fit a 1000 cc canister. Additionally there may be retractable arms on the case suitable for securing the EVR to the bed rails during patient transfers. An easy to carry handle will also be incorporated.

With the flow meter 101 of the SAWS, an automatic shut-off system can be placed that will sound an alarm and cut suction whenever a dangerous rate of fluid removal is recorded (e.g., 50 cc/min or 200 cc/10 min, or other parameter set by the individual provider). Various algorithms for response can be engineered to meet customer specifications. For example, immediately following dressing placement, this alarm can be suspended for a period, as there typically is a larger amount of fluid suctioned in the first 5 minutes of use.

There have been occasions in the use of conventional negative pressure systems where patients nearly exsanguinated in their hospital bedrooms because a vessel injury in the vicinity of the conventional device ruptured and arterial bleeding was suctioned up by the device. The conventional VAC systems have no means for recording the rate of flow of fluid from the wound. The only alarm that is generated in this situation is a "Full Canister" alarm, however this may not be activated until the patient has already lost 1-2 or more units of blood. The SAWS incorporates a liquid flow detecting sensor that will activate alarms for high flow rate at certain levels. Default levels will be set at manufacturing, however the device will have a menu access that allows the individual provider to set his or her own desired parameters. In addition to protecting against this rare, but potentially lethal event, a flow meter will provide the physician with an automated measure of the one value that needs to be recorded whenever a drainage system is used on the body—the amount of fluid removed. Outputs for traditional time periods (e.g., 8 hours or shift and 24 hours) can be displayed on the LCD screen. Automating outputs will eliminate this traditionally tedious nursing task and improve the accuracy of this data point. Accurate recording of fluid outputs from trauma patients with large open wounds or burns is very important.

Various embodiments of SAWS cycles through a low suction state rather than a zero suction state during intermittent suction mode. Intermittent suction (ramping from high to low vs. maintaining a constant set suction level) has been shown in animals to be most effect. However, this mode of therapy is often painful for patients, as the suction is reapplied it forces the sponge or wound filler against the wound. The conventional machines reduce to zero suction during intermittent mode cycling, thus producing the most pain. The dressing sponge fills with air and then contracts again when the full suction is resumed.

Since various embodiments of the SAWS intermittent suction mode does not reach zero, it helps to reduce the pain associated with this mode of negative pressure therapy. Reducing or eliminating the pain previously associated with the intermittent mode may encourage use of this mode, which may in turn improve the efficacy of negative pressure therapy. Likewise the ramp up interval, whether at the beginning of continuous mode therapy or with each intermittent mode cycle, will be controllable by the physician, or may be set to a default value (e.g., 5 to 30 seconds). In some embodiments the default ramp up interval may be set to 15 seconds, to allow more gradual increase in negative pressure as the device turns on. In addition, the SAWS device has a timer for recording the time of use, an important parameter for the physician. The timer also provides a means for automating rental time use, which is an important form of distribution for this device. Lastly, the LCD display has an area that displays the current time. The conventional devices do not have similar clocks or timers.

Various embodiments of SAWS use wall suction as its primary vacuum source, which removes the noisy vacuum generating process from the room. The SAWS unit may be connected to the wall suction source with a connector configured for such purpose. The use of wall suction greatly improves patient satisfaction, especially at night when the intermittent buzz of the vacuum unit on conventional devices disturbs sleep. Further, the use of wall suction can avoid frequent device alarms which may be due to overloading the vacuum motor of conventional devices. The vacuum motors of conventional devices are designed to be small in order to be mobile. Consequently, they have a limited suction capacity, especially when compared to the wall suction source. This means when leaks are detected and the pump is activated, the ability to respond and clear air quickly and efficiently may be compromised in conventional devices. Further, various embodiments of the SAWS use brushless vacuum motors as their portable and back-up vacuum source. These motors tend to be stronger, more efficient and quieter than conventional motors.

Conventional devices rely solely on an internal vacuum motor for suction. One drawback of this is that internal motors generate a monotonous buzz when they are active. Additionally, since the body's tissues are constantly dumping dissolved gas into the open wound, the vacuum will leak, regardless of the adhesive seal on the dressing. In the normal course of events, this leak, if detected by conventional devices, causes the internal motor to be activated in an effort to generate sufficient suction to maintain the desired therapeutic level, thus producing an annoying noise. While this noise may seem minor, the buzzing from this noise in the middle of the night significantly disrupts sleep. The buzz evident in conventional systems is to be reduced in various embodiments of SAWS through the use of brushless motors. An additional consideration of the motor is size. The motors of conventional systems tend to be small in order to minimize the size for portability purposes. Small motors have a limited reserve, and when they are connected in parallel to several wounds simultaneously they may be unable to clear the air volume needed to continuously maintain therapeutic suction. Wall suction is produced by large generators located in the basement of the hospital, the vacuum from these generators is more than sufficient for the present purposes, and their noise is not heard in the patient's room.

The tubing system 105 in various embodiment of the present invention has been simplified, as compared to conventional devices, to remove connectors which were always difficult to use and threatened the sterility of the operative field. The tubing in conventional systems is difficult to work with because of poorly designed connectors that connect the sterile end of the tubing to the nonsterile end. This typically occurs about 3 feet from the wound. When you apply the wound vac during surgery on the lower extremities, this short distance of sterile tubing section can cause nonsterile parts of the tubing to rub on and off the sterile parts of the surgical drapes, thus violating the sterile field. In various embodiments of the present invention these connectors are eliminated, while in other embodiments the connectors are moved farther away from the wound (e.g., four feet, five feet, or at least greater than three feet) to avoid the danger of compromising the sterile field. Various embodiments of SAWS do not require that central portions of the tubing to be connected by the physician. By contrast, conventional systems require the tube connecting to the wound to be connected to the tube traveling to the collection canister. The connector on conventional systems is difficult to use, and more importantly, it typically winds up resting on the edge of the sterile operative field. In this position, the connector, which is handled by the circulating OR nurse (thus contaminated) when the tubes are connected, can slide on and off the sterile OR field, creating potential breaks in the sterile field.

The tubing used in the SAWS system is arranged to provide a vacuum path to the regulated vacuum source, e.g., either the wall vacuum source or a vacuum motor (vacuum pump). The SAWS tubing may be off-the-shelf surgical tubing, sterile packed for application in the OR. The collection canister may be off-the-shelf as well, so long as the proper size is available, e.g., 1,000 cc. At the distal (wound) end of the tubing is a specially designed bilayer wound interface chamber 107. This is the means by which the tubing connects with the dressing. This chamber 107 allows for dispersion of the vacuum effect more equally over the extent of the dressing. Further, the chamber 107 may be configured with two appendaged tubes with drainage holes in them. These flexible, small tubes can be aimed and placed by the surgeon down long and narrow wound tracts, like those seen in wounds sustained from gunshots or improvised explosive devices. This helps to avoid the creation of occult deep space infections that occur in devices that do not offer this feature. If these tracts do not exist in the wound, then the tubing need not be used in the dressing.

In addition to functioning as a negative pressure wound dressing, the SAWS device can perform other functions. For example, for particularly painful wounds, intermittent doses of dilute local anesthetic could be run through the instillation system to reduce the pain. Lastly, the SAWS can be used without the tubing and wound filler dressing. Instead deep closed drains, like those placed with elective surgeries, can be hooked to the system and insure that a constant, regulated vacuum is being maintained. At the same time, the output for these drains can be automatically recorded. Since the EVR is a reusable device, this improved surgical drain concept can be used with little to no additional cost over that of the simple drains currently being used, which use manually applied bulb suction and require the nurse to record outputs.

Figure 2:
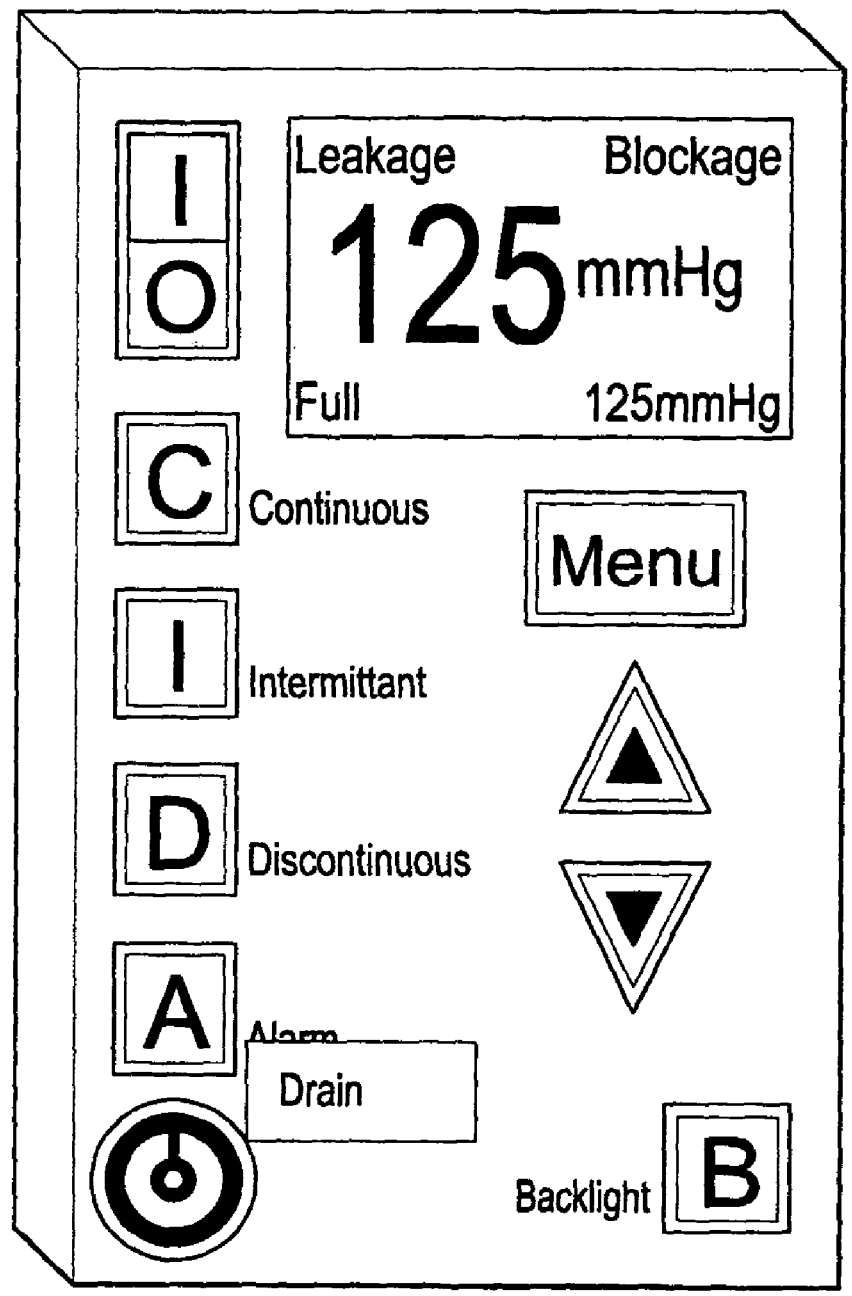
FIG. 2 depicts the electronic-programmable vacuum regulator (EVR) in accordance with various exemplary embodiments of the SAWS.
Figure 3:
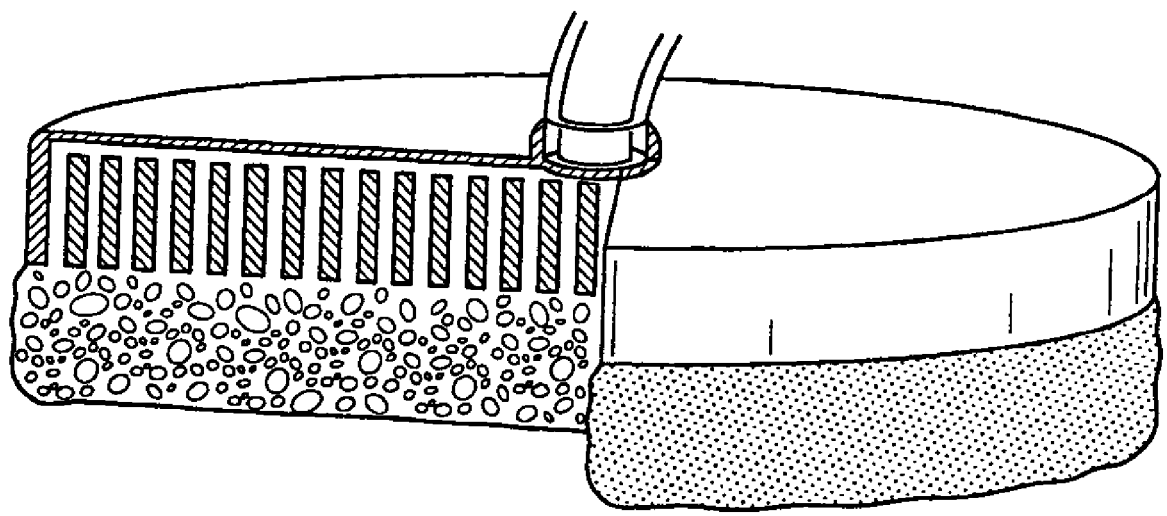
FIG. 3 depicts a cutaway view of the tubing interface chamber in accordance with various exemplary embodiments of the SAWS.

FIG. 2 depicts an exemplary embodiment 200 of the electronic-programmable vacuum regulator (EVR) for the SAWS. The electronic-programmable vacuum regulator (EVR) is the human interface with the SAWS device, and as such, is connected or otherwise has access to the vacuum path between the wound interface chamber and the regulated vacuum source. Various embodiments of the EVR contain an automated pressure valve that is controlled by internal software. This valve may be opened and closed in response to two pressure sensors that continuously monitor the negative pressure (vacuum) being applied to the wound. The intake end of the valve is typically configured to accept flow from either the hospital wall vacuum source or from an on-board brushless vacuum motor. Typically, the primary vacuum source for this device is the wall vacuum source. The on-board motor is there as a back-up should the primary source fail. Additionally, it will serve as the primary source when patients need mobility within the hospital. A connector is provided on the SAWS device for connection to the wall vacuum source.

The EVR has an LCD screen that displays various parameters such as: current actual pressure in the dressing, programmed or desired pressure, alarms and alarm status, time, and output. These parameters are discussed in the following paragraph. In various embodiments the front face of the EVR is configured with an LCD display of approximately 3"×1" size, with touch panel buttons. The buttons include an up arrow, down arrow, on/off, menu, enter and backlight button as shown in FIG. 2. These are used to program specific features and adjust the items displayed on the LCD screen.

The EVR displays the current actual pressure in the dressing, as determined by the SAWS dual pressure sensing technique which allows accurate and continuous pressure monitoring at the wound, with a back-up approximation measurement being taken in the tubing. The wound level pressure sensor allows the SAWS system to directly record the negative pressure at the wound, rather than approximating it by only measuring the tubing pressure, as is done in conventional systems.

The EVR also displays the programmed or desired pressure. The physician generally sets the desired parameter based on clinical use and experience within a predetermined safe-range. One reason for two different pressure displays is that, in practice, when there are leaks or problems with the system the actual pressure may not be the same as the desired pressure. If this state exists longer than a predetermined amount of time (e.g., 15 seconds), an alarm will alert the healthcare provider of this situation, which is likely due to a leak. The SAWS has a unique automated leak response algorithm that automatically increases suction in the system briefly when a leak is detected. This reaction will typically re-seal the leak in the adhesive seal. This automated response obviates the need for the provider to evaluate the system, thus reducing the total number of alarms and the amount of labor required to maintain the therapy. In the event that the leak persists or recurs immediately, then the leak alarm engages and the provider will have to address the situation. The provider can then come and evaluate the situation. Typically, when a leak occurs there will be an audible failure (hissing noise) in the wound dressing seal and additional occlusion adhesive dressing can be applied. In rare instances when the system continues to fail, the dressing can be removed at bedside and an "old fashioned" cotton gauze dressing can be applied.

Various embodiments of the SAWS device is equipped with a number of alarms and displays the alarms as well as the alarm status. For example, alarms may be provided for: leak (lost suction, with continued airflow), blockage (reduced suction, with diminished or absent airflow), canister full and high flow rate (e.g., >50 cc/10 min, >100 cc/30 min, or other safety parameters that can be programmed by the user). The combination of these alarms and their sensors will detect system failures that can occur with vacuum dressing therapy. Alarms will typically be configured to blink on the LCD display and alarm tones will also sound, until the EVR is assessed by a provider. In addition to displaying alarms and alarm status the SAWS displays the time as well. This time display serves as a consistent time piece for the provider, conveniently available for recording usage time.

The SAWS has memories for recording various parameters at predetermined or preset intervals. For example, the 8 hr and 24 hr output from the wound may be recorded automatically and displayed on the LCD screen.

Power for the SAWS may be supplied by an ordinary wall socket, with an optional internal rechargeable (e.g., lithium) battery, for power in case of power failure or when the unit needs to be used a mobile environment. The tubing and wound dressing are all disposable and will be packaged sterilely, but can be applied in a clean, nonsterile fashion depending on the operational environment. Typically, the EVR is a non-disposable capital piece that will be encased in a hardened enclosure that protects it from water or blunt force damage. Some embodiments of the EVR unit weigh less than 10 lbs and occupy a space of less than 6"×6"×6" in size. The EVR may be encased in high strength plastic, which is watertight and hardened to survive drops from up to 6' onto concrete. Typically, the casing and hardware of various SAWS embodiments is hardened to the extent that it is designed to withstand at least a 6 foot fall onto concrete. Additionally, it is watertight to avoid damage from moisture. This will expand the life span of the SAWS devices in both civilian and military uses.

Inside the SAWS case most embodiments include at least one circuit board, sensors for leakage, blockage, flow rate, a brushless vacuum motor, a rechargeable battery and an automated switch that can direct vacuum from the internal motor or the wall outlet through an automated pressure valve that opens/closes in response to changes in the wound dressing's negative pressure. Additionally, there are outlets (or adapters) to receive power from wall outlets. A standard wall vacuum outlet connector is typically positioned on the posterior aspect of the EVR. This connector may be configured to be retractable so that it can be retracted when the internal motor is being used.

FIG. depicts a cutaway view of the tubing interface chamber 300 in accordance with various exemplary embodiments of the SAWS. The chamber 300 is the chamber 107 of FIG. 1. The tubing interface chamber of SAWS is bilayer, which maximizes the dispersion of the vacuum effect to all aspects of the wound similar to the way a shower head disperses water. Additionally it has suction tubes that can be routed into deeper portions of the wound (not shown). These modular suction tubes are integral to the function of the interface chamber component. The combined modes of vacuum application to the wound filling material and wound bed, ensure the most symmetric distribution of vacuum to the wound. This, in turn, allows for the most optimal and complete drainage of the entire wound, which reduces the risk of occult infection. To further reduce the risk of occult infection in narrow deep tracts of wounds, the modular accessory suction tubes can be positioned into these tracts. Conventional devices have no such ability.

The custom designed SAWS wound interface chamber may be embodied as a dual-layer plastic air chamber with columns of plastic separating the 2 layers into uniform air channels. Either end of this elliptically shaped (to match the longitudinal contour of most wounds) interface chamber may be provided with docking ports for 8" long flexible drainage tubes with multiple perforations along their length. These accessory drains can be positioned into narrow or deep parts of the wound, to improve suction to these areas. These accessory drains are can be excluded, if they are not needed. These accessory drainage tubes can be routed by the surgeon to areas of the wound that need more focused suction, or more importantly to long narrow tracts in the wound. The conventional devices do not have these accessory drainage tubes, thus a situation can and does occur in which long narrow dead spaces are created in the depths of the wound. These dead spaces become locations were fluids and bacteria can coalesce. As a result, deep space infection can form under an otherwise well functioning VAC dressing of conventional devices.

The configuration of the SAWS tubing interface chamber is distinguished from the convention systems which use a "lily pad" tubing interface and do not perform as well at diffusing the vacuum. That is, the conventional negative pressure wound treatment devices use a monolayer flange that results in the central portion of the wound receiving the highest levels of suction while the periphery may not receive any. One conventional adapter, the KCI adaptor ("Lilly Pad"), is a sheet of plastic that is fused into the terminal end of the tubing. This conventional adaptor has plastic nubs that are placed on its distal surface. These are theoretically intended to disperse the vacuum as it hits the wound dressing. But since these nubs directly contact the moistened sponge, the dressing simply gets compressed into the nubs, thus negating any dispersion of vacuum. The SAWS uses a novel approach that disperses the air in stable chambers, like a shower head, ensuring that the vacuum is not simply dumped in the center of the dressing. By distributing the vacuum in the SAWS device, the periphery of the wound is exposed to the same level of vacuum as the central portion.

The SAWS dual pressure regulating sensors of various embodiments of the present invention are located in, or near, the wound, and in the tubing as well. The SAWS dual pressure sensing technique affords the accurate and continuous pressure monitoring useful for successful and reliable negative pressure wound therapy. This wound level pressure sensor allows the SAWS system to directly record the negative pressure at the wound, rather than approximating it by measuring the pressure in the tubing, as is done in conventional systems. This approximation based on tubing pressure done in conventional systems becomes more and more inaccurate in infected wounds where secretions are thicker. This sensing technique is very dependant on several factors (sponge thickness, wound contours, fluid consistency, or the like), factors that can all reduce the actual amount of therapeutic suction reaching the wound. The failure of pressure sensors in conventional devices to accurately control vacuum levels in the dressing is not sufficient to allow use in military air evacuation flights. Currently, the U.S. Army prohibits use of vacuum wound care devices during air evacuation operations due to the unreliability of the current art.

The wound level pressure sensor in the SAWS is located between the wound and the dressing. By contrast, the sole pressure sensor in conventional machines is housed in the tubing of the device. Thus, the pressure being sensed and displayed on the readout screen of conventional devices is an INDIRECT measure of the actual vacuum effect reaching the wound. The sensor measures the pressure in the column of air leading up to the sponge. This measured pressure is as an approximation of the actual negative pressure reaching the wound tissue. The thickness of the sponge, the depth and topography of the wound, the consistency of the secretions and several other factors all effect the accuracy of this approximation. The SAWS uses a disposable pressure sensing disc to provide feedback to the EVR. This DIRECT pressure measure will be used to guide therapy. For the wound level pressure measurement a pressure sensor disc is placed between the wound and the wound filler. It is typically connected to a wire running along the tubing. This will be the path of communication between this sensor and the EVR. Additionally, a pressure sensor in the EVR will detect the air pressure in the tubing. The software may be programmed to analyze the changes of pressure in the tubing and at the wound margins and an algorithm will be created that directs the automated pressure valve to open/close to respond to changes in the negative pressure levels.

A second sensing apparatus measures pressure in the column of air in the tubing. Data from this second pressure sensor will be used to determine leaks, blocks and integrated with the wound surface sensor data to regulate the vacuum level in the system. The SAWS dual sensor system tends to provide a more accurate pressure sensing mechanism, thus overcoming the failures of the conventional machines to maintain therapeutic vacuum levels during the transport of casualties. Currently, casualties are not allowed to be transported with the conventional KCI wound VAC dressings, as they have a high rate of failure. Failure of a negative pressure dressing system turns these dressings into infection producers instead of reducers. Several examples exist of this system failure, prior to the current policy of no transport with the KCI VAC dressings. This system will be designed specifically to overcome this significant drawback. Soldiers injured in Iraq are transported at least three times, and often several times, prior to making it to Echelon V care in the U.S. Each time, these soldiers have to be treated with "old fashioned" cotton dressings, which are painful, seep and smell. It has caused angst among US military surgeons who have to provide suboptimal dressings to our servicemen, while the Iraqi combatants that don't get transported, receive the state-of-the-art vacuum wound dressings immediately.

The wound filling material 301 of the SAWS system has been designed specifically for a negative pressure wound care application. This non-woven wound filler covers the wound surfaces, keeping the surfaces moist, while separating the wound from the overlying adhesive and providing a media which has preserved random pattern air channels that tends to disperse the vacuum equally to the wound surface. The wound filling materials used with conventional devices are typically off-the-shelf materials, and as such, are often subject to certain drawbacks because they are not specially designed for the purpose. For example, the KCI Wound V.A.C., uses an off the shelf filter sponge that is formed with open cell technology. This manufacturing process creates air filled cells throughout the sponge. When this conventional type of sponge is cut, these cells are randomly intersected. Due to the geometry of the cells, some cells are cut and leave dangling free edges, which can be captured by the wound tissue and remain trapped in the wound, when the dressing sponge is removed. This causes an inflammatory reaction occurs around these retained fragments of sponge. Moreover, the conventional sponge filters are typically 1" thick, which is too thick. The conventional filter sponges tend to clog with thick fluids. When this occurs the areas beneath these clogs do not get therapeutic levels of suction. For another conventional device, the Verstaile 1, it is recommended that cotton gauze dressing be used. Cotton is an absorbent and porous material, unlike the polymers used in the SAWS wound filler. Cotton products that remain in contact with the body for prolonged periods can harbor bacteria which produce toxins that can injure patients (e.g., toxic shock syndrome). Cotton gauze packing is typically not left in closed or sealed cavities in the body for this reason. By contrast, the wound filler 301 of various embodiments of the present invention is a non-woven polymer fiber that has no free dangling edges, thus obviating the aforementioned complications.

The SAWS specially designed non-woven wound filler material is placed on the open wound surface, after the wound has been surgically debrided. The filler has malleability properties similar to steel wool, which allow the material to be stretched from its resting, packaged state, to fill and match the contours of the wound without the need of surgical instruments to trim the material to fit. This novel material may be impregnated with specially complexed silver ion molecules that can deliver sustained antimicrobial effect. A special silver impregnated fine sheet netting can be placed between the wound filler and the wound surface to prevent in-growth of the wound tissue into the wound filler. This will extend the life of each dressing, which will reduce the overall number of dressings and operations to replace dressings. The silver impregnated fine mesh is particularly suitable for extended use applications (e.g., >3 days). An adhesive may be used to seal the dressing to the skin margins and create an airtight (or near airtight) environment for the vacuum dressing to work. This adhesive will secure the wound interface chamber to the wound filler, thus completing the vacuum circuit.

The sponges used with conventional devices were not designed specifically for negative pressure use. These conventional sponges are nonpliable—thus, scissors need to be used to cut the sponge to the exact contours of the wound. This contouring/shaping step is often the longest step in the entire wound dressing application process, using conventional systems. Likewise, the standard sponge used with conventional devices is too thick. Fluids clot within the sponge and block suction to areas of the wound. The novel SAWS wound filler addresses these problems through its design. Since the SAWS material is moldable, the surgeon can mold the dressing to fit the wound. The filler may be formed to be thin enough to cover the wound. Further, the thickness of the filler can easily be adjusted by the physician, without the need of surgical instruments. The SAWS wound filler material is pliable, but resists compression under typical conditions. For example, under vacuum, various embodiments retain a sufficient amount (e.g., 50%) of its thickness. Furthermore, the SAWS wound filler media has sufficient porosity to maintain adequate vacuum levels and drain fluids from the wound, e.g., >60%.

Various embodiments of the SAWS wound filler media are bio-compatible, having no inflammatory response. Moreover, the media is indestructible under normal conditions to the extent that the fibers of the media cannot be pulled free from the rest of the media. Various embodiments of the material are durable and do not dissolve due to contact with fluid or human tissue. The media is preferably stable in open air room conditions for up to 1 hour, and at room to body temperature indefinitely.

Figure 4:
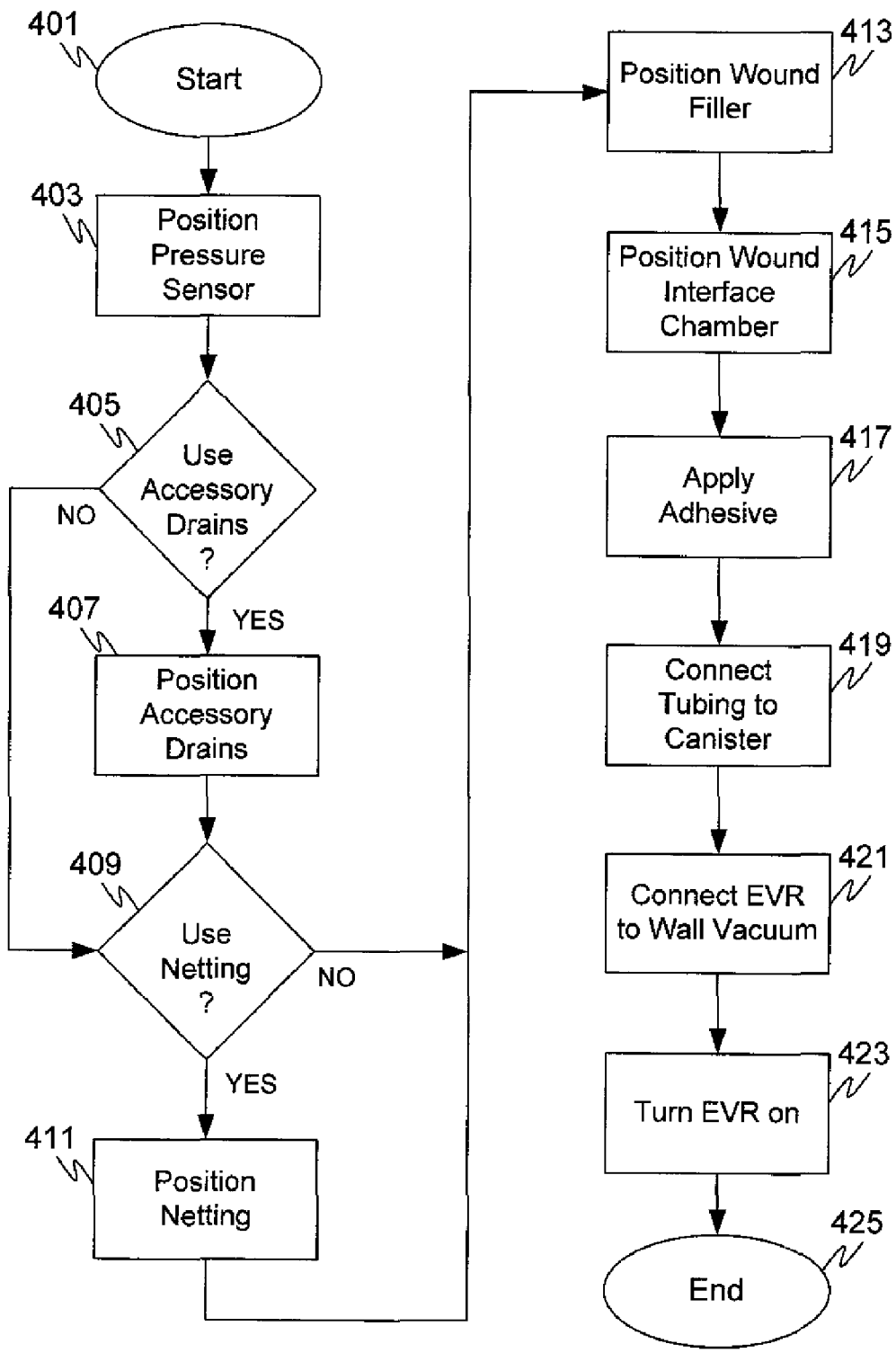
FIG. 4 is a flowchart of an exemplary method of using the SAWS system in accordance with various embodiments.

FIG. 4 is a flowchart of an exemplary method of using the SAWS system in accordance with various embodiments. The method begins in 401 and proceeds to 403. In 403 a pressure sensor disc is placed on the wound surface. Once the pressure sensor has been positioned the method proceeds to 405. In 405 it is determined whether accessory drains are to be used. If accessory drains are needed the method proceeds along the "YES" path to 407 and accessory drains are placed into deep, narrow portions of the wound. The proximal ends of these drains and the pressure sensor wire are then left out to the margins of the wound. Back in 405 if it is determined that no accessory drains are needed the method proceeds along the "NO" path to 409.

In 409 it is determined whether netting is to be used with the SAWS device, e.g., a silver impregnated fine sheet netting for use between the wound filler and the wound surface.

Netting is used in some situations to aid in preventing ingrowth of the wound tissue into the wound filler. If netting is to be used the method proceeds from 409 along the "YES" branch to 411 to position the netting. Once the silver impregnated netting is in place the method proceeds to 413. Alternatively, back in 409 if it is determined that no netting is to be used, the method proceeds along the "NO" path to 413.

In 413 the wound filler is laid on a clean open wound, over the sensor. (In some instances, over the optional netting.) The SAWS wound filler is a malleable, porous substance, as described above. The wound filler may be shaped to approximate the contours of the would. After the wound filler has been property positioned the method proceeds to 415. In block 415 the wound interface chamber is placed centrally over of the wound filler. In situations where accessory drains are used, their proximal ends are folded back over the wound filler and connected to their ports on the interface chamber. The pressure sensor wire is folded back over the wound filler and connected to its mating wire on the tubing. Once the wound interface has been placed on the wound filler and connected to the accessory drains (if any) the method proceeds to 417.

In 417 a clear adhesive is placed over the wound filler. The adhesive secures the wound filler and interface chamber to the surrounding normal skin, which has been shaved and coated with a sticky substance, to improve adhesion. Upon completing 417 the method proceeds to 419 to connect the canister. The proximal end of the tubing is thrown off the operative table and the circulating (nonsterile) OR nurse connects the tube to the 1000 cc collection canister. In 419 the EVR is connected to the canister and to the wall vacuum outlet. Once all components of the SAWS are in place, the method proceeds to 423 and the EVR is turned on and the therapy is started. A successfully sealed and functioning dressing is confirmed, prior to completion of the case in 425.

Various components and/or activities may be included or excluded as described above, or assembled/performed in a different order, with the invention still remaining within the scope of at least one exemplary embodiment. For example, in some embodiments the direct pressure sensor (positioned in block 403) may be placed over the screen netting, rather than directly on the wound. In some embodiments the EVR may be connected to the wall vacuum (block 421) before connecting it to the canister (block 419), or, alternatively, before any of the activities preceding it as depicted in FIG. 4. Those of ordinary skill in the art know that other such variations in implementing embodiments of the invention exist, and are within the scope of at least one exemplary embodiment.

The use of the word "exemplary" in this disclosure is intended to mean that the embodiment or element so described serves as an example, instance, or illustration, and is not necessarily to be construed as preferred or advantageous over other embodiments or elements. The description of the various exemplary embodiments provided above is illustrative in nature and is not intended to limit the invention, its application, or uses. Thus, variations that do not depart from the gist of the invention are intended to be within the scope of the embodiments of the present invention. Such variations are not to be regarded as a departure from the spirit and scope of the present invention.

What is claimed is:

1. A sub-atmospheric wound-care system for treating an open wound comprising:
   a connector configured to be connected to wall suction as a regulated vacuum source for developing a negative pressure;
   a flow rate meter configured to measure a flow rate of liquid removed from the wound;
   a pressure regulating sensor to be placed at a surface of the wound for directly measuring the negative pressure at the wound;
   a collection canister with volume level markings configured to collect said liquid removed from the wound; and
   a porous dressing positioned over the wound and over the pressure regulating sensor placed at the surface of the wound.

2. The sub-atmospheric wound-care system of claim 1, wherein the wall suction is a first regulated vacuum source, the system further comprising:
   a vacuum motor configured for use as a second regulated vacuum source; and
   a valve configured to be switched between the first regulated vacuum source and the second regulated vacuum source.

3. The sub-atmospheric wound-care system of claim 1, wherein the vacuum motor is a brushless vacuum motor.

4. The sub-atmospheric wound-care system of claim 1, further comprising:
   a wound interface chamber connected via a vacuum path to the regulated vacuum source; and
   a tube connected to the wound interface chamber;
   wherein the porous dressing is disposed between the wound interface chamber and the wound.

5. The sub-atmospheric wound-care system of claim 4, further comprising:
   an electronic-programmable vacuum regulator configured to access the vacuum path.

6. The sub-atmospheric wound-care system of claim 4, wherein the pressure regulating sensor is a first pressure regulating sensor, the system further comprising:
   a second pressure regulating sensor disposed in said tube for taking indirect measurements of the negative pressure at the wound.

7. The sub-atmospheric wound-care system of claim 1, wherein the porous dressing is configured to be sealed airtight over the wound.

8. The sub-atmospheric wound-care system of claim 1, wherein the porosity of the porous dressing is greater than 60%.

9. The sub-atmospheric wound-care system of claim 1, wherein the pressure regulating sensor is located between the porous dressing and the wound.

10. The sub-atmospheric wound-care system of claim 4, wherein the pressure regulating sensor is located between the wound interface chamber and the wound.

11. The sub-atmospheric wound-care system of claim 2, wherein the vacuum motor is battery operated.

12. The sub-atmospheric wound-care system of claim 1, further comprising:
    a first alarm configured to indicate that a predefined flow rate has been reached as detected by said flow rate meter;
    fluid level detection means for detecting a fluid level in the collection canister; and
    a second alarm configured to indicate that a predefined fluid level has been reached in the collection canister fluid level detection means.

13. The sub-atmospheric wound-care system of claim 1, wherein the pressure regulating sensor fits within a depression in the porous dressing arranged to expose the pressure regulating sensor to the surface of the wound.

14. The sub-atmospheric wound-care system of claim 1, wherein the flow rate meter is further configured to detect accelerated fluid outflow from the wound.

15. A system configured to apply negative pressure to a wound, the system comprising:
- a wound interface chamber configured to hold a porous dressing over the wound;
- a flow rate meter configured to measure a flow rate of liquid removed from the wound interface chamber;
- a pressure regulating sensor positioned between the porous dressing and a surface of the wound for directly measuring the negative pressure at the wound; and
- a tube connecting the wound interface chamber and a collection canister for said liquid removed from the wound.

16. The system of claim 15, wherein the pressure regulating sensor fits within a depression in the porous dressing arranged to expose the pressure regulating sensor to the surface of the wound.

17. The system of claim 15, further comprising:
- a connector configured to be connected to wall suction as a regulated vacuum source for developing the negative pressure.

18. The system of claim 15, wherein the pressure regulating sensor is a first pressure regulating sensor, the system further comprising:
- a tube disposed between the wound interface chamber and a vacuum source;
- a second pressure regulating sensor disposed in said tube for taking indirect measurements of the negative pressure at the wound.

19. The system of claim 15, further comprising:
- a first alarm configured to indicate a predefined flow rate has been reached as detected by said flow rate meter;
- fluid level detection means for detecting a fluid level in the collection canister; and
- a second alarm configured to indicate that a predefined fluid level has been reached in the collection canister fluid level detection means.

20. The system of claim 15, wherein the flow rate meter is further configured to detect accelerated fluid outflow from the wound.

* * * * *